United States Patent
Forster et al.

(10) Patent No.: US 10,452,875 B2
(45) Date of Patent: Oct. 22, 2019

(54) USING RFID DEVICES INTEGRATED OR INCLUDED IN THE PACKAGING OF MEDICAL DEVICES TO FACILITATE A SECURE AND AUTHORIZED PAIRING WITH A HOST SYSTEM

(71) Applicant: Avery Dennison Retail Information Services, LLC, Westborough, MA (US)

(72) Inventors: Ian J. Forster, Chelmsford (GB); Michael G. Ginn, Danbury (GB)

(73) Assignee: AVERY DENNISON RETAIL INFORMATION SERVICES, LLC, Mentor, OH (US)

( * ) Notice: Subject to any disclaimer, the term of this patent is extended or adjusted under 35 U.S.C. 154(b) by 0 days.

(21) Appl. No.: 15/312,418

(22) PCT Filed: May 21, 2015

(86) PCT No.: PCT/US2015/031891
§ 371 (c)(1),
(2) Date: Nov. 18, 2016

(87) PCT Pub. No.: WO2015/179595
PCT Pub. Date: Nov. 26, 2015

(65) Prior Publication Data
US 2017/0091498 A1    Mar. 30, 2017

Related U.S. Application Data

(60) Provisional application No. 62/001,778, filed on May 22, 2014.

(51) Int. Cl.
*G06F 19/00*     (2018.01)
*G06K 7/10*      (2006.01)
(Continued)

(52) U.S. Cl.
CPC ..... *G06K 7/10297* (2013.01); *G06K 19/0723* (2013.01); *G06K 19/07758* (2013.01); *G16H 40/63* (2018.01)

(58) Field of Classification Search
CPC .. G06F 19/3456; G06F 19/327; G06F 19/322; G06F 19/326; G06F 19/321;
(Continued)

(56) References Cited

U.S. PATENT DOCUMENTS

| 7,872,574 B2 | 1/2011 | Betts et al. |
| 7,889,070 B2 | 2/2011 | Reeves et al. |

(Continued)

FOREIGN PATENT DOCUMENTS

| CN | 201537085 | 8/2010 |
| CN | 101822535 | 9/2010 |
| TW | M398897   | 3/2011 |

OTHER PUBLICATIONS

International Search Report and Written Opinion prepared for PCT/US2015/031891 dated Aug. 31, 2015.
(Continued)

*Primary Examiner* — Jamara A Franklin
(74) *Attorney, Agent, or Firm* — Avery Dennison Retail Information Services, LLC

(57) ABSTRACT

A system and method for linking a medical device with a smart device is provided. The system includes a medical device, a smart device, a package encasing the medical device and an RFID device integrated into the packaging and associated with the medical device. The method for linking the medical device to a smart device includes removing the medical device from the packaging and applying it to a person, presenting the RFID device to the smart device, reading the RFID device with the smart device and using information obtained from the RFID device to estab-
(Continued)

lish communications between the smart device and the medical device.

20 Claims, 3 Drawing Sheets

(51) Int. Cl.
   *G06K 19/07* (2006.01)
   *G16H 40/63* (2018.01)
   *G06K 19/077* (2006.01)

(58) Field of Classification Search
   CPC ..... A61B 90/98; A61B 90/90; A61B 2562/08;
       A61B 5/4839; A61B 50/30; A61M 5/002;
       A61M 5/16827
   USPC ............. 235/385; 705/2, 22, 28; 340/539.12
   See application file for complete search history.

(56) References Cited

U.S. PATENT DOCUMENTS

| | | | |
|---|---|---|---|
| 7,969,307 | B2 | 6/2011 | Peeters |
| 7,978,062 | B2 | 7/2011 | LaLonde et al. |
| 2005/0258242 | A1 | 11/2005 | Zarembo |
| 2007/0185739 | A1 | 8/2007 | Ober et al. |
| 2007/0272746 | A1* | 11/2007 | Ortiz .................. G06K 17/00 235/385 |
| 2007/0273517 | A1 | 11/2007 | Govind |
| 2009/0043253 | A1 | 2/2009 | Podaima |
| 2009/0112072 | A1 | 4/2009 | Banet et al. |
| 2010/0194541 | A1 | 8/2010 | Stevenson |
| 2010/0198034 | A1 | 8/2010 | Thomas et al. |
| 2010/0315225 | A1 | 12/2010 | Teague |
| 2011/0022411 | A1 | 1/2011 | Hjelm et al. |
| 2011/0105854 | A1 | 5/2011 | Kiani et al. |
| 2011/0175735 | A1 | 7/2011 | Forster |
| 2011/0224564 | A1 | 9/2011 | Moon et al. |
| 2011/0254687 | A1 | 10/2011 | Arponen et al. |
| 2012/0029390 | A1 | 2/2012 | Colborn |

OTHER PUBLICATIONS

Halperin et al. Security and Privacy for Implantable Medical Devices. IEEE Pervasive Computing [Online] 2008, vol. 7, Issue 1, pp. 30-39.

Liolios et al. An Overview of Body Sensor Networks in Enabling Pervasive Healthcare and Assistive Environments. Proceedings of the 3rd International Conference on Pervasive Technologies Related to Assistive Environments [Online] 2010.

Moore. The potential use of radio frequency identification devices for active monitoring of blood glucose levels. Journal of Diabetes Science and Technology [Online] 2009, vol. 3, Issue 1, pp. 180-183.

Shahriyar et al. Intelligent Mobile Health Monitoring System (IMHMS). International Journal of Control and Automation [Online] 2009, vol. 2, No. 3, pp. 13-28.

Trappey et al. Develop Patient Monitoring and Support System Using Mobile Communication and Intelligent Reasoning. Proceedings of the 2009 IEEE International Conference on Systems, Man, and Cybernetics [Online] 2009, pp. 1195-1200.

* cited by examiner

USING RFID DEVICES INTEGRATED OR INCLUDED IN THE PACKAGING OF MEDICAL DEVICES TO FACILITATE A SECURE AND AUTHORIZED PAIRING WITH A HOST SYSTEM

CROSS-REFERENCE TO RELATED APPLICATION

The present application is a 371 of International Application No. PCT/US2015/031891, which was published in English on Nov. 26, 2015, and claims the benefit of U.S. Provisional Patent Application No. 62/001,778 filed on May 22, 2014, each of which is incorporated herein by reference in its entirety.

FIELD OF THE INVENTION

The present invention is in the field of using Radio Frequency Identification (RFID) Devices. More particularly, the invention is directed to using RFID devices to facilitate a secure and authorized pairing with a host system when packaging medical devices.

BACKGROUND OF THE INVENTION

The use of radio frequency identification (RFID) to identify an item is well known. Typical radio frequency identification (RFID) devices or integrated circuits include a microprocessor, also known as a microchip, electrically connected to an antenna. Alternatively, the microchip is first attached to a pad, referred to as a strap or interposer. The strap is then attached to the antenna.

The microprocessor stores data, which can include identifying data unique to a specific item, which is transmitted to an external receiver for reading by an operator and processing of the item. RFID devices are particularly useful in identifying, tracking and controlling items such as packages, pallets, and other product containers. The location of each item can be tracked and information identifying the owner of the item or specific handling requirements can be encoded into the RFID and later read by a scanning device capable of decoding and displaying the information.

Conventional RFID devices are either active or passive. Active indicates that the devices have an internal power source and passive indicates that the device is without an internal power source. Passive RFID devices are energized by the electromagnetic field produced by the reader.

Accordingly, RFID devices can be attached to items and the identifying information received can be processed for various reasons in a variety of manners. RFID devices are particularly useful in identifying, tracking and controlling items such as pallets, packages and individual product containers. For example, RFID labels are often applied to the exteriors of individual containers through the use of pressure sensitive adhesives.

As noted above, RFID devices are generally categorized as labels or tags. RFID labels are RFID devices that are adhesively or otherwise have a surface attached directly to objects. RFID tags, in contrast, are secured to objects by other means, for example by use of a plastic fastener, string or other fastening means.

RFID devices can retain and transmit enough information to uniquely identify individuals, packages, inventory and the like. RFID tags and labels also can be characterized as to those to which information is written only once (although the information may be read repeatedly), and those to which information may be written during use. RFID devices, either active or passive, may include sensors, such as temperature, shock, presence of specific liquids or gases or other environmental parameters, such as exposure to sterilization, such as ethylene oxide or gamma radiation.

Near-field communication (NFC) is a type of radio frequency communication technology, operating at about 13.56 MHz and at bandwidth of about 2 MHz, which allows for read-only and read-write communications between a NFC-enabled RF device reader and a NFC-enabled device. NFC operation is based on inductive coupling between two loop antennas, which allows for sharing of power and data between NFC-enabled devices. Typically, for proper operation, the distance between a NFC-enabled reader and a NFC-enabled device needs to be under about 20 centimeters.

RFID can offer various benefits to the medical industry. It can be used for identification, labeling, tracking and as a method to improve and streamline various processes. The addition of sensor capability can also monitor the environmental conditions that the medical product has been exposed to, for example temperature, which may affect the proper operation of the medical device. The RFID device may include ferro-electric memory, which is resistant to radiation, specifically gamma rays that are used in sterilization for medical devices.

A need still exists for RFID Devices integrated or included in the packaging of medical devices to facilitate a secure and authorized pairing with a host system.

BRIEF SUMMARY OF THE INVENTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

One embodiment includes a system for linking at least one medical device with a smart device. In a particular embodiment, the system includes at least one medical device, a smart device, at least one package encasing the at least one medical device, and at least one RFID device integrated into the packaging and associated with the at least one medical device.

One embodiment includes a method of linking a medical device with a smart device. First, obtain a system that includes a medical device, a smart device, a package encasing the medical device, and an RFID device integrated into the packaging and associated with the medical device. Next, remove the medical device from the packaging and apply it to a person and/or patient. Next, present the RFID device to the smart device and read the RFID device with the smart device. Finally, use the information obtained from the RFID device to establish communications between the smart device and the medical device. The ability to link the device may be inhibited or a warning may be given if the medical device has been exposed to conditions that may make the device unsuitable for use.

Other features and advantages of the present invention will become apparent to those skilled in the art from the following detailed description. It is to be understood, however, that the detailed description of the various embodiments and specific examples, while indicating preferred and other embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

These, as well as other objects and advantages of this invention, will be more completely understood and appreciated by referring to the following more detailed description of the presently preferred exemplary embodiments of the invention in conjunction with the accompanying drawings, of which.

DETAILED DESCRIPTION OF THE INVENTION

Figure 1:
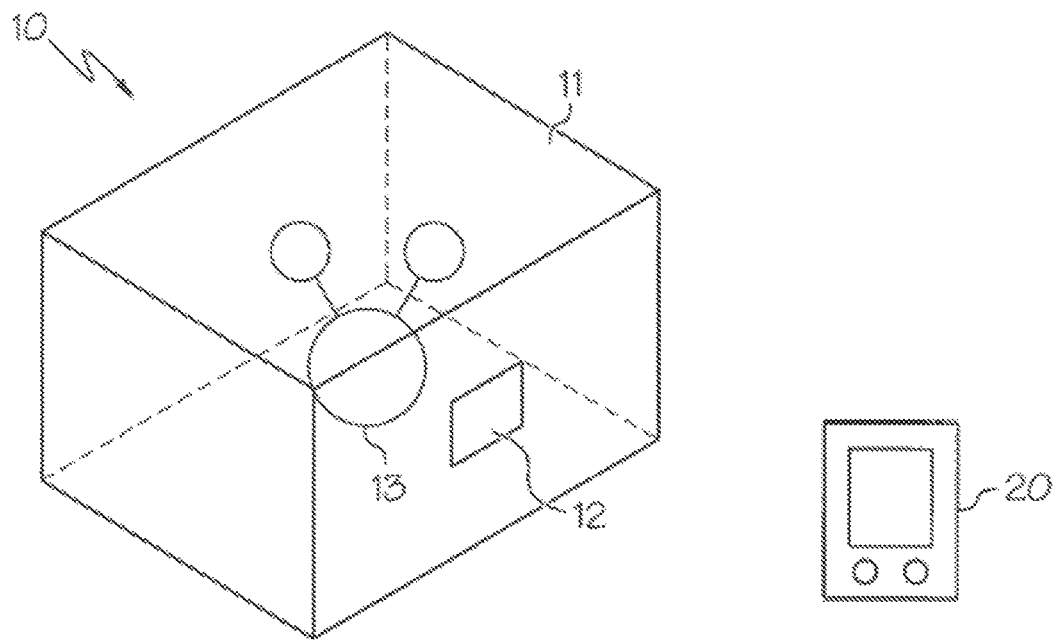
FIG. 1 depicts one embodiment of packaged state of the RFID device system.

The apparatuses and methods disclosed in this document are described in detail by way of examples and with reference to the figures. Unless otherwise specified, like numbers in the figures indicate references to the same, similar, or corresponding elements throughout the figures. It will be appreciated that modifications to disclosed and described examples, arrangements, configurations, components, elements, apparatuses, methods, materials, etc. can be made and may be desired for a specific application. In this disclosure, any identification of specific shapes, materials, techniques, arrangements, etc. are either related to a specific example presented or are merely a general description of such a shape, material, technique, arrangement, etc. Identifications of specific details or examples are not intended to be, and should not be, construed as mandatory or limiting unless specifically designated as such. Selected examples of apparatuses and methods are hereinafter disclosed and described in detail with reference made to FIGURES.

According to this invention, an RFID device or tag can be associated or packaged with a medical device and can assist in achieving authorized and controlled connection to a host system.

Medical Device

The medical device of this invention can be any known in the art. The medical device can be a sensor, including a wearable sensor. The medical device can be any type of medical patch, including a monitoring patch.

The medical patch can use one or more sensors. The sensing device can be included in a wound care bandage as well.

Physiological sensors can be a part of the medical device. The connection provides for either a time resolved or context based assessment of data from the various sensing elements.

A physiological sensing device when used in cooperation with a wound sensing device can provide valuable historical data that will help physicians or medical specialists make accurate diagnosis. Such a cooperative device can additionally empower patients or their care providers to seek early intervention to their problem.

A number of physiological parameters are used to monitor lifestyle and well being of individuals. Examples of physiological parameters include electrocardiogram (ECG or EKG), blood pressure, beat, heart rate, respiration, lung volume, blood circulation, body temperature, oxygen saturation, gait, activity etc. depending on the context and prognosis. In situations of non-medical monitoring such as athletic, exercise, or weight loss related activities, these parameters provide insight into usefulness of such activities. In the case of medical monitoring, these parameters can provide life saving information such as emergency intervention, adjustment of medication or response of a patient during the course of an acute care. Acute care generally refers to outpatient, in-hospital or life threatening emergency intervention procedures.

In one embodiment, the data from sensors on the medical device are collected and integrated over time to provide a current status along with any future trend(s). This data can be communicated to the smart device after the communications are established between the smart device and the medical device. In another embodiment, the data from sensors on the medical device is collected at specific intervals. In yet another embodiment, the data is collected when initiated by the smart device.

The preferred sensing patch or sensor can be used in cooperation with medication administration. Active or passive drug delivery with transdermal or oral modes of delivery can be used. The sensing results can be used to measure the effectiveness of a particular dosing regimen or its effectiveness on a particular patient condition. The preferred sensing patch can be used in a home setting for self awareness and/or management of a chronic condition, and data can be easily uploaded to a primary care giver for future action. In cases where more than one combination of drugs are used, the patch can be used for providing insights on drug efficacy through measurement of one or more physical or chemical parameters using the preferred sensing patch. Medication can also be included in the sensing patch.

In cases where the patch utilizes an on-board processor and a power source, the battery can be a coin cell, thin-film printed or combination thereof. The power source can additionally be based on an electromagnetic energy harvesting mechanism. For example, the power could originate from the small voltage generated during the interrogation of passive RFID devices in the presence of an RFID reader.

The sensing patch system can be linked and monitored during the course of care with a medical service provider, medical insurance, public health system (for example, Medicare in USA) and the like.

The patch based chemical and physical sensors can be used beneficially to improve patient outcome or compliance in case of trauma or chronic conditions requiring monitoring of the previously noted indications. The patch based sensing elements, e.g. physical and/or chemical, can be used in a hospital, nursing home, long term care or home care situations by beneficially using wireless technologies to communicate information to and from the patient to a physician or care provider.

The sensing patch can be attached to a patient through the use of a pressure sensitive adhesive, an activatable adhesive, or other fastening means such as a string or hook-and-loop fasteners (also known as VELCRO).

In a particular embodiment, the medical device is a monitoring patch designed to transmit readings via a data communications link to a host system.

RFID Device

The RFID device of the current invention can be any of those know in the art. RFID devices are generally categorized as labels or tags. RFID labels are RFID devices that adhesively or otherwise have a surface that is attached directly to objects. RFID tags, in contrast, are secured to objects by other means, for example by use of a plastic fastener, string or other fastening means.

An RFID device consists of an RFID inlay, or an antenna and microchip.

An RFID inlay includes an inlay substrate and an antenna thereupon. The inlay substrate may be any of a variety of suitable materials. The suitable materials for the inlay substrate 104 may include materials that are flexible, and are suitable for use in roll-to-roll processes. The inlay substrate may be a piece of material that has been separated from a webstock or sheetstock.

Examples of suitable materials for the inlay substrate 104 include, but are not limited to, high Tg polycarbonate, polyethylene terephthalate (PET), polyarylate, polysulfone, a norbornene copolymer, poly phenylsulfone, polyetherimide, polyethylenenaphthalate (PEN), polyethersulfone (PES), polycarbonate (PC), a phenolic resin, polyester, polyimide, polyetherester, polyetheramide, cellulose acetate, aliphatic polyurethanes, polyacrylonitrile, polytrifluoroethylenes, polyvinylidene fluorides, HDPEs, poly(methyl methacrylates), a cyclic or acyclic polyolefin, or paper.

The antenna may be an antenna in any of a variety of suitable configurations. The antenna may be made of a conductive material, such as a metallic material. The antenna may be formed on the inlay substrate by any of a variety of methods. For example, the antenna may be formed from conductive ink that is printed or otherwise deposited on the inlay substrate. Alternatively, the antenna may be formed from metal deposited on the inlay substrate by any of a variety of suitable, known deposition methods, such as vapor deposition. As a further alternative, the antenna may be part of a web of antenna material that is adhered to the substrate by suitable means, for example, by use of a suitable adhesive in a lamination process. The web of a plurality of antennas may be made from, for example, copper, silver, aluminum or other thin conductive material. The web of antennas may be on a film, coated paper, laminations of film and paper, or other suitable substrate. As yet another alternative, the antenna may be formed by selective removal of metal from a metal layer, for example, using known lithography processes. It will be appreciated that other suitable means, for example, electroplating, may be used to form the antenna on the inlay substrate.

RFID devices include active tags and labels, which include a power source, and passive tags and labels, which do not. The RFID device of the current invention can be active or passive. In one preferred embodiment, the RFID device is an NFC enabled device. NFC, as it operates via near field magnetic coupling, is, depending on the standard used, capable of two way communications, but at relatively short range compared to RFID operating at UHF frequencies, depending on the size and type of UHF antenna used.

The RFID devices used can include various forms of security protocols as implemented in NFC compatible chips made by NXP under the trade name Mifare.

RFID devices enable communication at a predetermined preferred frequency of operation of the RFID chip. There are three normal frequency ranges for RFID devices, Low, High and Ultra High. Low frequency is typically in the range of 125-134 kHz. High Frequency is typically at 13.56 MHz and Ultra High is usually in the range of 860 to 960 MHz. The preferred frequency of operation may be at high frequency or NFC (Near Field Communication) frequency. UHF frequencies may be used with RFID devices implementing security protocols, such as those enabled by the EPC Gen2V2 standard, or other means including the use of private and public key encryption of unique data stored in the RFID device. To limit operating range if required, the UHF device can be made small compared to an equivalent device operating at LF or HF, and operate in the near field region or radiating near field region at UHF frequencies.

The authorization tags may be multiple or single use. In one embodiment the tag/device is single use, in that after the link has been made, the reader system erases or otherwise deletes the data needed to pair the patch to a host system, preventing the unit from being re-used.

The RFID device may include and/or store various types of data. For instance, the RFID device may include and/or store data such as when the medical device was first made and when it should be used by to ensure that it cannot be used unless it is safe to do so. The RFID device may contain manufacturing information about the medical device. The RFID device may have data stored in it relating to sensor values, either taken at the time of reading or relating to the history of the device; this data may be processed to provide a good/bad indication either in the RFID device or by the host system.

Data Communication Link

The data communications link can be any known in the art. In one embodiment, the data communications link is a Bluetooth link. In another embodiment, the link is established through a WIFI connection.

According to at least one exemplary embodiment, methods, systems and apparatuses for communication may be shown and described. These can include the use of near field communications (NFC), for example a NFC RFID device that is able to communicate with a NFC-enabled device, for example a mobile device, smart phone or any other device having a scanner or reader, e.g., a PC or a tablet. Further, any number of NFC RFID devices may be associated with any desired medical products, allowing NFC-enabled devices to read or scan the NFC RFID devices and access data or information provided by the NFC RFID devices, which may be associated with products optionally coupled to the NFC RFID devices. Thus, one tag or device can be associated with a single medical product or multiple devices can be used with multiple medical products or multiple devices on a single medical product with each device offering potentially different information or different levels of the same information or service.

The data communications link may be enabled by a RFID device/code unique identifier. This is required if additional content needs to be retrieved from a web server in order for the server to know which additional enriched content needs to be sent back to the application that is requesting it. The unique id which may be following a specific pattern can also be used to verify that the device/code has a valid id and will not be redirected to a malicious site or application. It also assures that the device/code will be supported by the application.

In one embodiment, when the medical device and its preferred embodiments are used in conjunction with a wireless intermediary device, the communication between the medical device and the handheld is a closed loop communication. Closed loop communication particularly refers to the communication of measured parameter values to a remote facility through the internet for example and in return, receiving an advice or actionable instruction(s) to further improve the patient condition and treatment. The advice or actionable instruction can be returned or displayed to the wireless intermediary device or could follow through additional means such as using voicemail. The remote facility could provide care recommendation by using a live medical professional (physician, specialist, nurses, trained technicians etc.) or by using suitable screening programs. Information generated using the preferred device is sent to a professional site, such as a medical professional or a well established screening program. The information is then evaluated by the professional site. Actionable instruction is sent back to the patient or to a care giver through the hand held device, if needed. The patient and care giver can then follow the instruction. This process can also be carried out through the internet.

Referring generally to exemplary FIGS. 1-4 and the associated descriptions, methods, systems and apparatuses for data transfer and communication may be described. Exemplary embodiments utilizing data transfer may allow for the transmission of data from a device, such as a radio frequency identification (RFID) tag or other device capable of transmitting data, for example utilizing near field communication (NFC), such as a NFC RFID tag or device.

Smart Device

The smart device of the present invention may be any known in the art. In some embodiments the smart device is a phone or tablet. In some further exemplary embodiments, the smart device is a mobile device, which may be a mobile phone, a smart phone, tablet, PC or other device with a scanner or reader, may be capable of reading a NFC RFID tag or device, collecting information and data from the NFC RFID tag or device, and redirect a user of the mobile device to a website, software application or application store.

The host system can be any known in the art. In one embodiment, the host system is a Smart Phone or Tablet PC. In one embodiment, the Smart Phone or tablet PC has an integrated reader, operating at HF frequencies, that is capable of reading secure RFID tags or devices conforming to the Near Field Communications standard. In another embodiment, the host system is an RFID reader which operates at the HF or UHF frequencies.

By reading a RFID device supplied with the monitoring patch, the smart phone can be paired with the patch to receive and transmit data and, if required, relay such data by a longer range communication method, for example WiFi, Wimax, 3G or 4G to a host system. The RFID device can also cause the phone to request authorization from a host system for use of the medical device, and transmit an activation or other code to the device as required.

The invention is illustrated in the following description and diagrams.

In FIG. 1 the basic components of the system 10 are shown; a medical device 13 can be packaged in container 11. In one embodiment container 11 is a sterile package. The packaging can be of any material and shape known in the art. Non-limiting examples include different types of polymeric substrates. The polymeric layer or layers of the polymeric substrate may be any sheet or box forming, film forming, or substrate forming material, preferably a flexible material such as paper, synthetic paper, non-woven sheets, fabric sheets, polymeric film or sheets, and the like.

In one embodiment, the at least one polymeric layer includes a polyester film, particularly polyethylene terephthalate (PET) films, poly(ethylene 2,6-naphthalene dicarboxylate) (PEN) films, and polypropylene films. In a preferred embodiment, at least one polymer layer includes a polypropylene film layer.

A secure RFID device 12 capable of communicating via NFC with a reader system is integrated into the packaging of the container 11. The component also includes a smart device 20, such as a phone, including an NFC reader and a communication system capable of bidirectional or unidirectional data transfer to the patch. The smart device is not limited to a phone and can be any known device in the art capable of bidirectional or unidirectional data transfer to the patch. Optionally the Smart device may include other data transfer links such as 2,3 and 4G, Wimax, WiFi etc.

Figure 2:
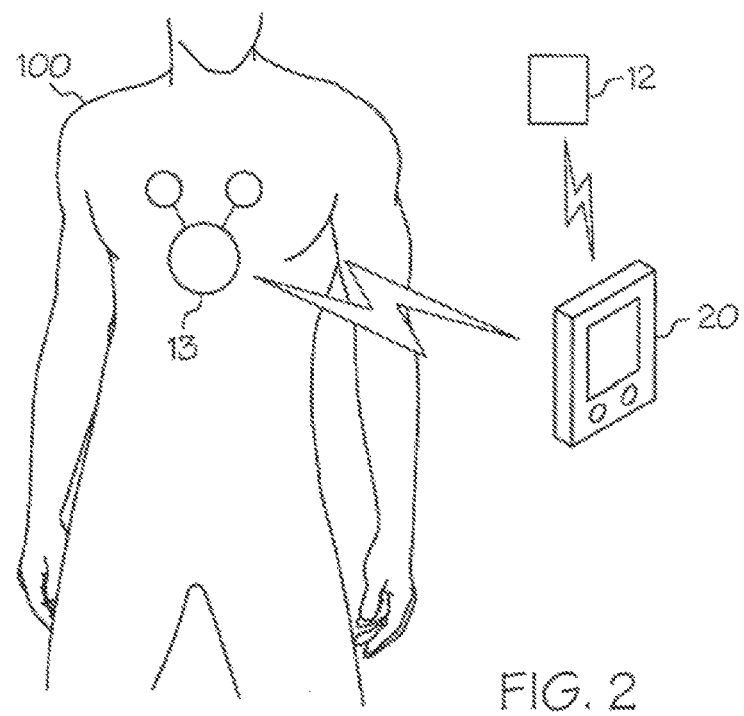
FIG. 2 depicts one embodiment of the deployed/installed state of the RFID device system.

In FIG. 2 the system 10 in its deployed/initialization state is shown. The medical device is attached to a patient 100, and the RFID device 12 from the packaging 11 is presented to the smart device 20, allowing it to be read. Using information obtained from the RFID device 12, the device 20 can establish communications with the medical device 13 and activate it if required.

Figure 3:
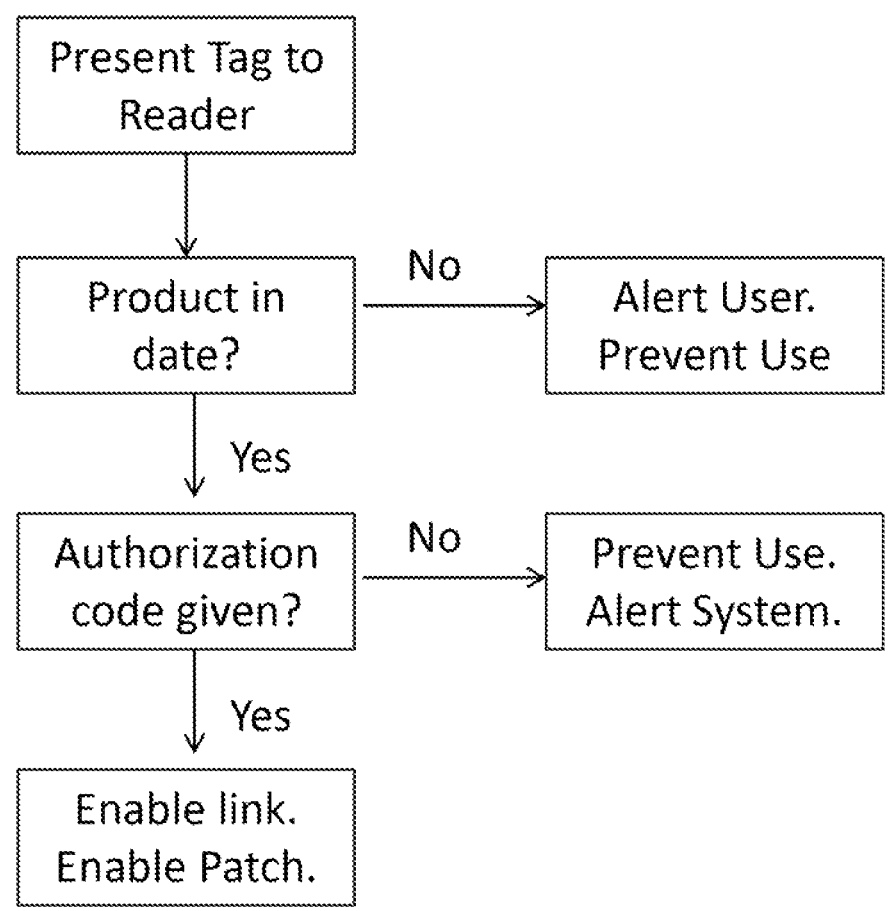
FIG. 3 depicts the basic flow diagram for association of a medical package and device with an RFID device.

In FIG. 3 a flow diagram of one option for the basic activation is shown wherein the RFID device is a RFID tag. When the tag is presented critical information, such as use by date, is read and it is determined if the product can be used. Then, optionally, the system can require further authorization, for example a code or a code presented by showing the NFC reader a second tag associated with a medical professional authorized to use the device. In the event that all tests are satisfactorily passed, the communication link is activated, allowing the device to pair with the patch. Alternatively the patch may be in communication with the host but unable to operate until a code or codes are transferred via the link.

Figure 4:
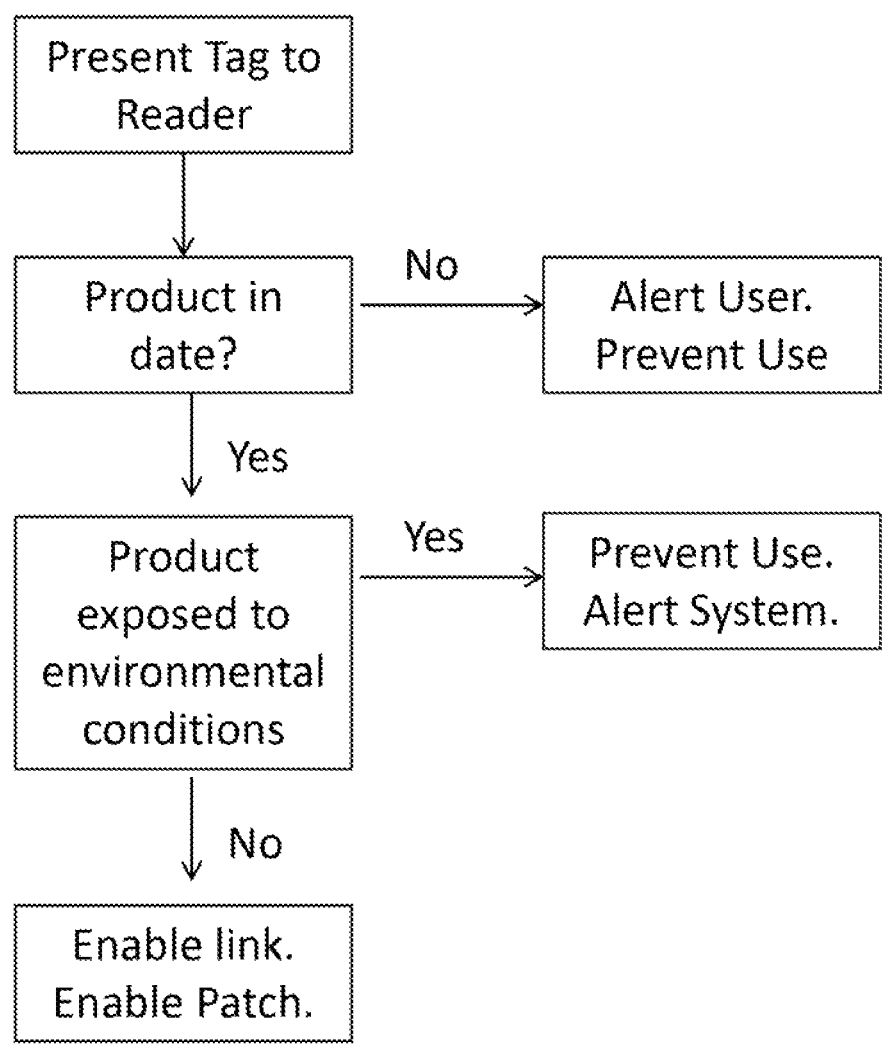
FIG. 4 depicts a flow diagram of one option for an activation including the analysis of data from a sensor.

In FIG. 4 a flow diagram of one option for activating including the analysis of data from a sensor is shown.

FIGS. 3 and 4 both have the medical device as a patch. The medical device can be any known in the art, as previously described in the application. FIGS. 3 and 4 also have the RFID device as a tag. The RFID device can also be any known in the art, as previously described in the application.

It will thus be seen according to the present invention a highly advantageous system using RFID devices integrated or included in the packaging of medical devices to facilitate a secure and authorized pairing with a host system has been provided. While the invention has been described in connection with what is presently considered to be the most practical and preferred embodiment, it will be apparent to those of ordinary skill in the art that the invention is not to be limited to the disclosed embodiment, and that many modifications and equivalent arrangements may be made thereof within the scope of the invention, which scope is to be accorded the broadest interpretation of the appended claims so as to encompass all equivalent structures and products.

The inventors hereby state their intent to rely on the Doctrine of Equivalents to determine and assess the reasonably fair scope of their invention as it pertains to any apparatus, system, method or article not materially departing from but outside the literal scope of the invention as set out in the following claims.

What is claimed is:

1. A method of linking a medical device with a smart device including:
    obtaining a system for linking a medical device with a smart device that includes:
        a medical device;
        a smart device;
        a package encasing the medical device; and
        an RFID device integrated into the package encasing and associated with the medical device;
    removing the medical device from the package encasing and applying to a person;
    presenting the RFID device to the smart device;
    reading the RFID device with the smart device;

using information obtained from the RFID device to establish communications between the smart device and the medical device.

2. The method of claim 1, wherein the medical device is a wearable sensor.

3. The method of claim 1, wherein the medical device is a sensing patch.

4. The method of claim 3, wherein the sensing patch is used in cooperation with medication administration.

5. The method of claim 1, wherein the smart device is a smart phone or tablet.

6. The method of claim 1, wherein the RFID device is a NFC enabled device.

7. The method of claim 1, wherein the RFID device operates at a frequency of about 13.6 MHz.

8. The method of claim 1, wherein the RFID device is an active device.

9. The method of claim 1, wherein the RFID device is a passive device.

10. The method of claim 1, wherein the package is sterile packaging.

11. The method of claim 1, wherein the RFID device is single use.

12. The method of claim 1, wherein the RFID device is multiple use.

13. The method of claim 1, wherein the RFID device includes data about the medical device.

14. The method of claim 13, wherein the information is manufacturing information.

15. The method of claim 1, further including the step of activating the medical device.

16. The method of claim 1, wherein the communications is enabled by a unique identifier.

17. The method of claim 1, wherein the communications are closed loop communication.

18. The method of claim 1, further including the step of using the smart device to collect data from the medical device.

19. The method of claim 18, wherein the data is collected at specific intervals.

20. The method of claim 18, wherein the data is collected when initiated by the smart device.

* * * * *